(12) United States Patent
Reiter

(10) Patent No.: US 9,980,702 B2
(45) Date of Patent: *May 29, 2018

(54) WIREBONDING FIXTURE AND CASTING MOLD

(71) Applicant: Volcano Corporation, San Diego, CA (US)

(72) Inventor: Michael Reiter, San Diego, CA (US)

(73) Assignee: Volcano Corporation, San Diego, CA (US)

( * ) Notice: Subject to any disclaimer, the term of this patent is extended or adjusted under 35 U.S.C. 154(b) by 1197 days.

This patent is subject to a terminal disclaimer.

(21) Appl. No.: 14/132,597

(22) Filed: Dec. 18, 2013

(65) Prior Publication Data

US 2014/0187962 A1    Jul. 3, 2014

Related U.S. Application Data

(60) Provisional application No. 61/747,599, filed on Dec. 31, 2012.

(51) Int. Cl.
| | |
|---|---|
| *A61B 8/00* | (2006.01) |
| *H03H 3/02* | (2006.01) |
| *B06B 1/06* | (2006.01) |
| *H01L 41/23* | (2013.01) |
| *B29C 45/14* | (2006.01) |

(Continued)

(52) U.S. Cl.
CPC .......... *A61B 8/4483* (2013.01); *B06B 1/0651* (2013.01); *B06B 1/0688* (2013.01); *B29C 45/14418* (2013.01); *B29C 45/14467* (2013.01); *B29C 45/14639* (2013.01); *H01L 41/23* (2013.01); *H03H 3/02* (2013.01); *A61B 8/12* (2013.01); *A61B 8/445* (2013.01); *B29C 45/03* (2013.01); *B29C 45/34* (2013.01); *B29C 45/401* (2013.01); *Y10T 29/42* (2015.01); *Y10T 29/4957* (2015.01)

(58) Field of Classification Search
None
See application file for complete search history.

(56) References Cited

U.S. PATENT DOCUMENTS

| | | |
|---|---|---|
| 4,158,910 A | 6/1979 | Hanas et al. |
| 4,668,460 A | 5/1987 | Ongena |

(Continued)

FOREIGN PATENT DOCUMENTS

| | | | |
|---|---|---|---|
| WO | WO 2012/075129 | 6/2012 | |
| WO | WO 2012/075153 | 6/2012 | |
| WO | WO 2012075129 A2 * | 6/2012 | ............... A61B 8/12 |

OTHER PUBLICATIONS

International Searching Authority/European Patent Office, "Communication—Supplementary European Search Report," for European Application No. 13869083.9, dated Aug. 4, 2016, 12 pages.

(Continued)

*Primary Examiner* — Long V Le
*Assistant Examiner* — Yi-Shan Yang

(57) ABSTRACT

The present disclosure involves a method and apparatus for attaching two electrical dies by wire bonding and then encasing the assembly in a protective casting that works by arranging two dies into a fixture conducive to wire bonding. Doped epoxy may be immediately dispensed over the assembly to form a near-net-shape protective cover, or Drive Can.

27 Claims, 7 Drawing Sheets

(51) Int. Cl.
    *B29C 45/03*    (2006.01)
    *A61B 8/12*     (2006.01)
    *B29C 45/34*    (2006.01)
    *B29C 45/40*    (2006.01)

(56) References Cited

U.S. PATENT DOCUMENTS

| | | | |
|---|---|---|---|
| 5,176,140 A | | 1/1993 | Kami et al. |
| 5,243,988 A | | 9/1993 | Sieben et al. |
| 5,546,948 A | | 8/1996 | Hamm et al. |
| 5,770,941 A | | 6/1998 | Van Den Berg |
| 5,935,502 A | | 8/1999 | Ferri et al. |
| 5,943,558 A | | 8/1999 | Kim et al. |
| 6,196,824 B1 | | 3/2001 | Foltuz et al. |
| 6,423,102 B1 | * | 7/2002 | Fukunaga ............ B25B 11/005 269/21 |
| 6,641,540 B2 | | 11/2003 | Fleischman et al. |
| 8,277,380 B2 | * | 10/2012 | Daft .................... B06B 1/064 600/407 |
| 2003/0003630 A1 | | 1/2003 | Iimura et al. |
| 2004/0214371 A1 | * | 10/2004 | Mahmood ............ H01L 21/565 438/106 |
| 2006/0011701 A1 | | 1/2006 | Duan et al. |
| 2006/0185429 A1 | * | 8/2006 | Liu .................... B60C 23/0408 73/146.5 |
| 2008/0304729 A1 | | 12/2008 | Peszynski |
| 2009/0192388 A1 | | 7/2009 | Yamada et al. |
| 2010/0160788 A1 | * | 6/2010 | Davies ................ A61B 5/0084 600/467 |
| 2010/0168583 A1 | | 7/2010 | Dausch et al. |
| 2010/0179430 A1 | | 7/2010 | Sano et al. |
| 2012/0056511 A1 | | 3/2012 | Sakai |
| 2012/0262796 A1 | | 10/2012 | Ferguson et al. |
| 2013/0168740 A1 | * | 7/2013 | Chen .................. B81C 1/00238 257/254 |

OTHER PUBLICATIONS

International Search Report and Written Opinion received in corresponding Patent Cooperation Treaty Application No. PCT/US2013/078280 dated Apr. 21, 2014, 12 pages.

* cited by examiner

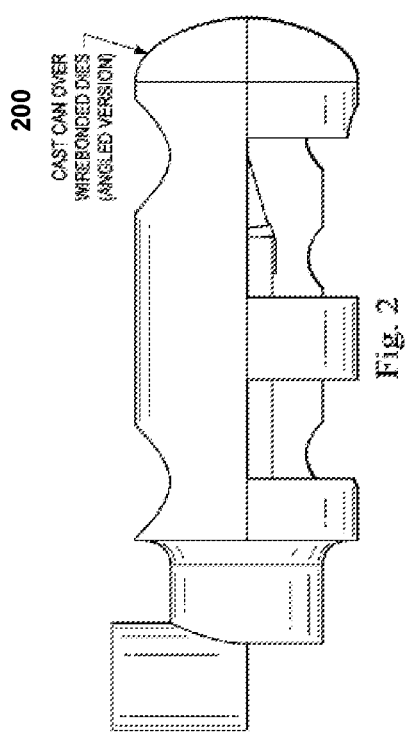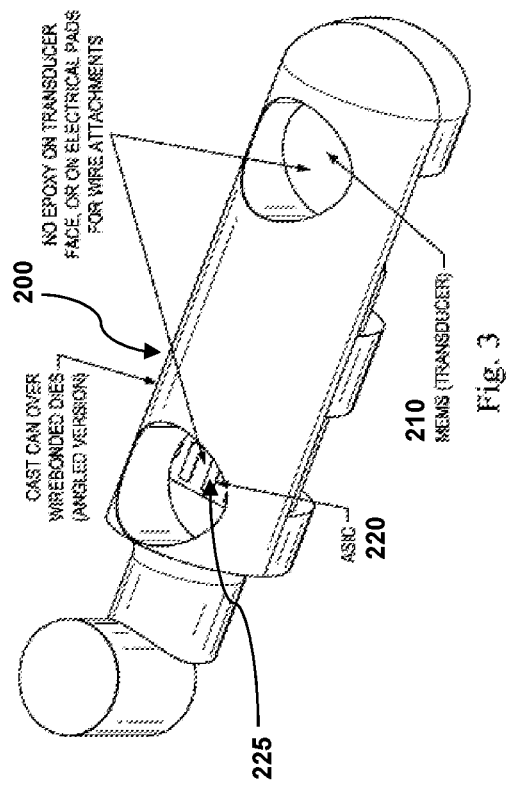

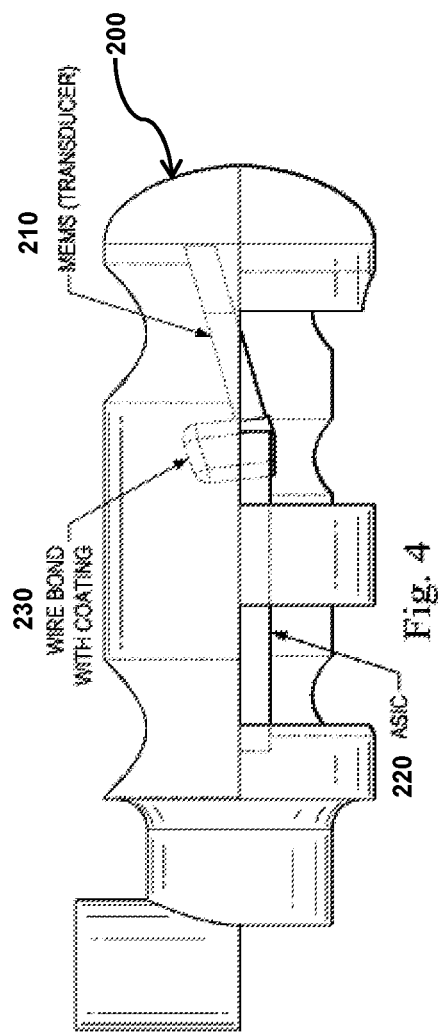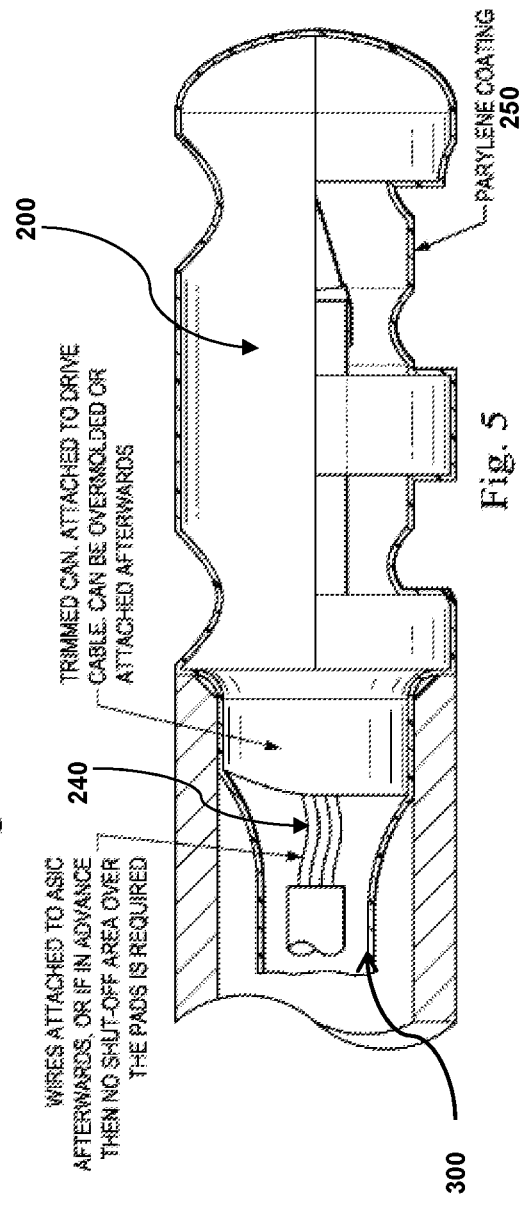

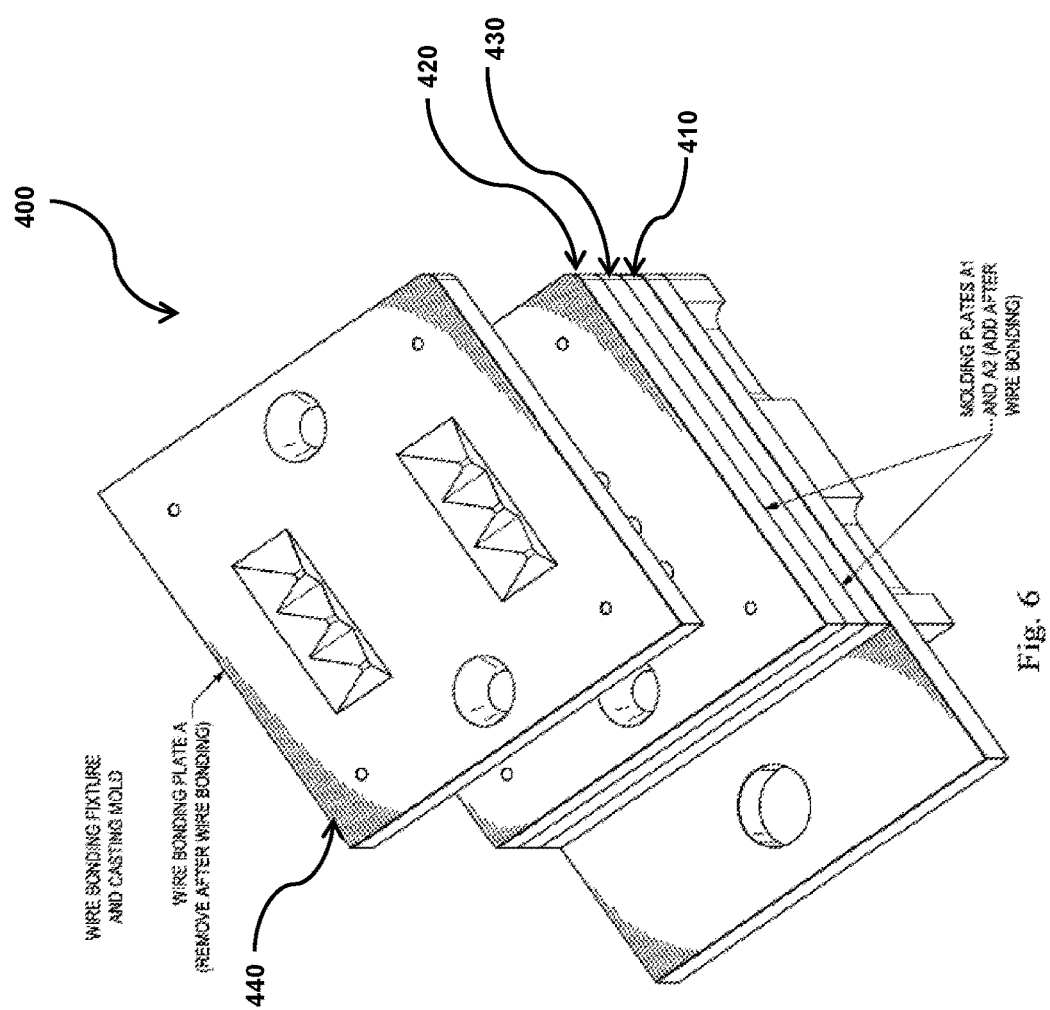

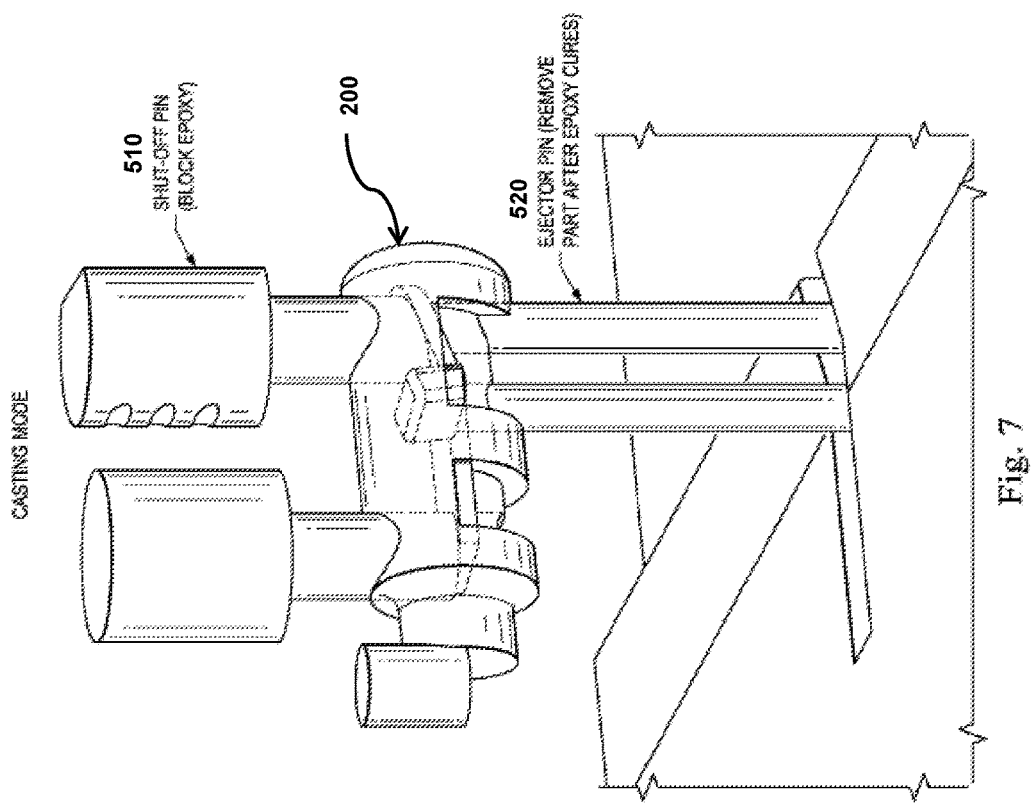

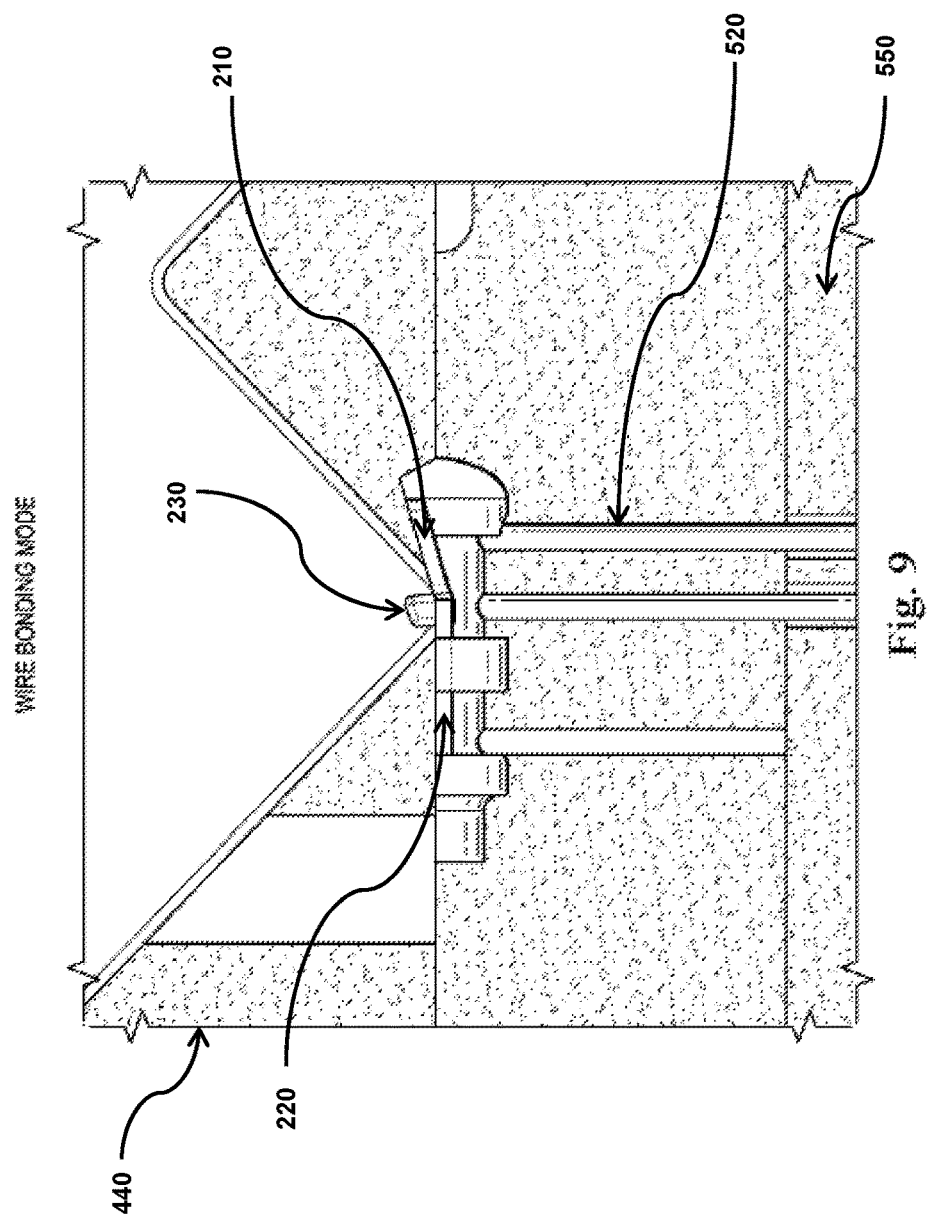

WIREBONDING FIXTURE AND CASTING MOLD

CROSS-REFERENCE TO RELATED APPLICATIONS

This application claims priority to Provisional Patent Application No. 61/747,599, filed Dec. 31, 2012, and entitled "WIREBONDING FIXTURE AND CASTING MOLD," the disclosure of which is hereby incorporated by reference in its entirety

TECHNICAL FIELD

The present disclosure relates generally to intravascular ultrasound (IVUS) imaging, and in particular, to a wirebonding fixture and casting mold for an IVUS ultrasound transducer, such as a piezoelectric micromachined ultrasound transducer (PMUT), used for IVUS imaging.

BACKGROUND

Intravascular ultrasound (IVUS) imaging is widely used in interventional cardiology as a diagnostic tool for assessing a vessel, such as an artery, within the human body to determine the need for treatment, to guide intervention, and/or to assess its effectiveness. An IVUS imaging system uses ultrasound echoes to form a cross-sectional image of the vessel of interest. Typically, IVUS imaging uses a transducer on an IVUS catheter that both emits ultrasound signals (waves) and receives the reflected ultrasound signals. The emitted ultrasound signals (often referred to as ultrasound pulses) pass easily through most tissues and blood, but they are partially reflected by discontinuities arising from tissue structures (such as the various layers of the vessel wall), red blood cells, and other features of interest. The IVUS imaging system, which is connected to the IVUS catheter by way of a patient interface module, processes the received ultrasound signals (often referred to as ultrasound echoes) to produce a cross-sectional image of the vessel where the IVUS catheter is located.

IVUS catheters typically employ one or more transducers to transmit ultrasound signals and receive reflected ultrasound signals. However, conventional catheters may create a separate wire-die sub assembly that is then placed into a stainless steel shell (also referred to as a can) and then epoxied with a specially doped epoxy. This shell or can is shaped to prevent acoustic echo off of the metal can. Preventing separation of the transducer from the can is important. However, this is not always achieved by conventional techniques.

Therefore, while conventional methods of producing and assembling transducers are generally adequate for their intended purposes, they have not been entirely satisfactory in every aspect.

SUMMARY

The present disclosure provides a method and apparatus for attaching two electrical dies by wire bonding and then encasing the assembly in a protective casting that works by arranging two dies into a fixture conducive to wire bonding. Doped epoxy may be immediately dispensed over the assembly to form a near-net-shape protective cover, or Drive Can.

Both the foregoing general description and the following detailed description are exemplary and explanatory in nature and are intended to provide an understanding of the present disclosure without limiting the scope of the present disclosure. In that regard, additional aspects, features, and advantages of the present disclosure will become apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIGS. 2-9 are diagrammatic perspective views and cross-sectional views of the various fixtures and tools used in transducer fabrication and assembly according to various aspects of the present disclosure.

DETAILED DESCRIPTION

Figure 1:
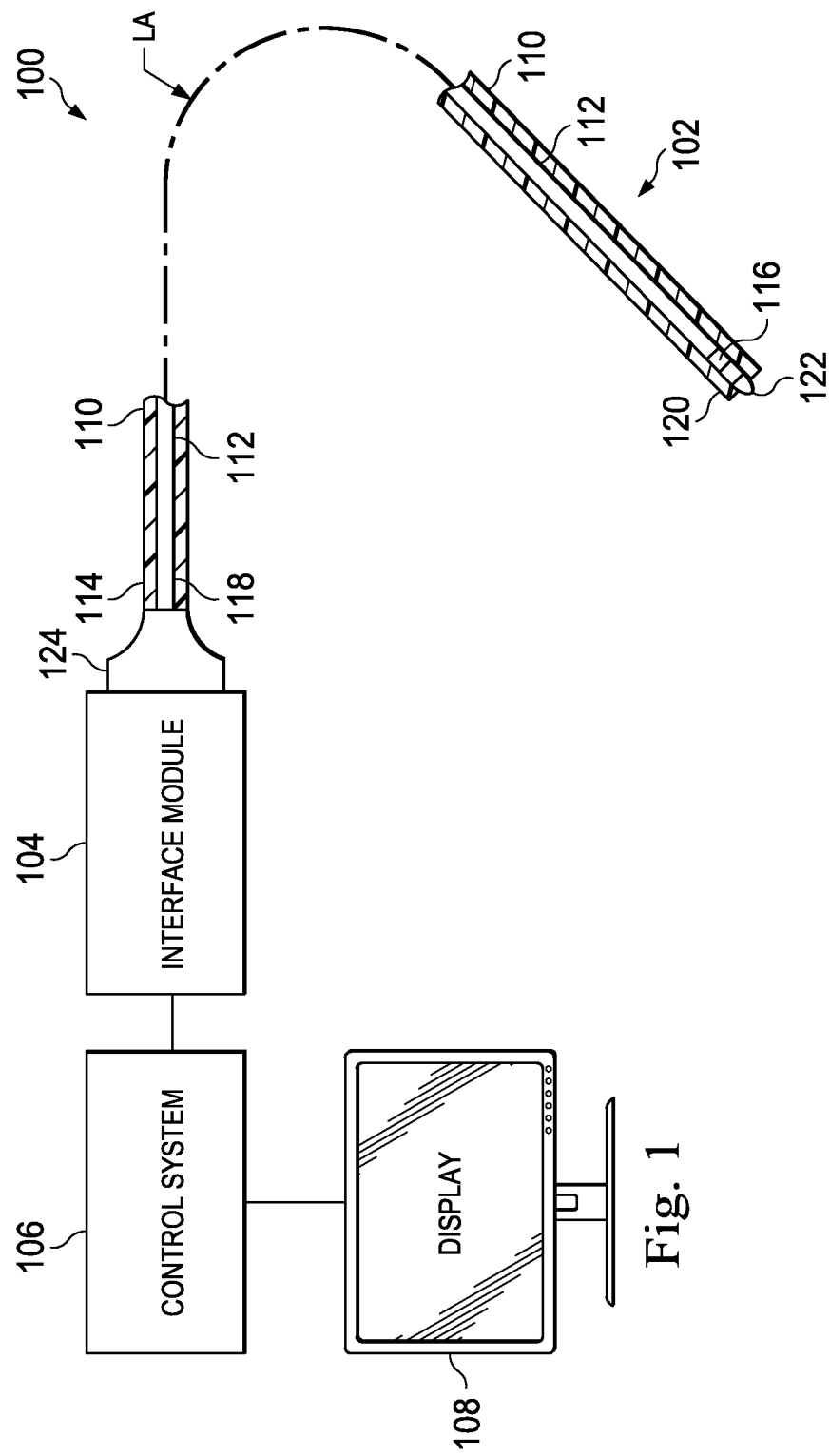
FIG. 1 is a schematic illustration of an intravascular ultrasound (IVUS) imaging system according to various aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, the present disclosure provides an ultrasound imaging system described in terms of cardiovascular imaging, however, it is understood that such description is not intended to be limited to this application. In some embodiments, the ultrasound imaging system includes an intravascular imaging system. The imaging system is equally well suited to any application requiring imaging within a small cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

There are primarily two types of catheters in common use today: solid-state and rotational. An exemplary solid-state catheter uses an array of transducers (typically 64) distributed around a circumference of the catheter and connected to an electronic multiplexer circuit. The multiplexer circuit selects transducers from the array for transmitting ultrasound signals and receiving reflected ultrasound signals. By stepping through a sequence of transmit-receive transducer pairs, the solid-state catheter can synthesize the effect of a mechanically scanned transducer element, but without moving parts. Since there is no rotating mechanical element, the transducer array can be placed in direct contact with blood and vessel tissue with minimal risk of vessel trauma, and the solid-state scanner can be wired directly to the imaging system with a simple electrical cable and a standard detachable electrical connector.

An exemplary rotational catheter includes a single transducer located at a tip of a flexible driveshaft that spins inside a sheath inserted into the vessel of interest. The transducer is typically oriented such that the ultrasound signals propagate generally perpendicular to an axis of the catheter. In the typical rotational catheter, a fluid-filled (e.g., saline-filled) sheath protects the vessel tissue from the spinning transducer and driveshaft while permitting ultrasound signals to freely propagate from the transducer into the tissue and back. As the driveshaft rotates (for example, at 30 revolutions per second), the transducer is periodically excited with a high voltage pulse to emit a short burst of ultrasound. The ultrasound signals are emitted from the transducer, through the fluid-filled sheath and sheath wall, in a direction generally perpendicular to an axis of rotation of the driveshaft. The same transducer then listens for returning ultrasound signals reflected from various tissue structures, and the imaging system assembles a two dimensional image of the vessel cross-section from a sequence of several hundred of these ultrasound pulse/echo acquisition sequences occurring during a single revolution of the transducer.

FIG. 1 is a schematic illustration of an ultrasound imaging system 100 according to various aspects of the present disclosure. In some embodiments, the ultrasound imaging system 100 includes an intravascular ultrasound imaging system (IVUS). The IVUS imaging system 100 includes an IVUS catheter 102 coupled by a patient interface module (PIM) 104 to an IVUS control system 106. The control system 106 is coupled to a monitor 108 that displays an IVUS image (such as an image generated by the IVUS system 100).

In some embodiments, the IVUS catheter 102 is a rotational IVUS catheter, which may be similar to a Revolution® Rotational IVUS Imaging Catheter available from Volcano Corporation and/or rotational IVUS catheters disclosed in U.S. Pat. No. 5,243,988 and U.S. Pat. No. 5,546,948, both of which are incorporated herein by reference in their entirety. The catheter 102 includes an elongated, flexible catheter sheath 110 (having a proximal end portion 114 and a distal end portion 116) shaped and configured for insertion into a lumen of a blood vessel (not shown). A longitudinal axis LA of the catheter 102 extends between the proximal end portion 114 and the distal end portion 116. The catheter 102 is flexible such that it can adapt to the curvature of the blood vessel during use. In that regard, the curved configuration illustrated in FIG. 1 is for exemplary purposes and in no way limits the manner in which the catheter 102 may curve in other embodiments. Generally, the catheter 102 may be configured to take on any desired straight or arcuate profile when in use.

A rotating imaging core 112 extends within the sheath 110. The imaging core 112 has a proximal end portion 118 disposed within the proximal end portion 114 of the sheath 110 and a distal end portion 120 disposed within the distal end portion 116 of the sheath 110. The distal end portion 116 of the sheath 110 and the distal end portion 120 of the imaging core 112 are inserted into the vessel of interest during operation of the IVUS imaging system 100. The usable length of the catheter 102 (for example, the portion that can be inserted into a patient, specifically the vessel of interest) can be any suitable length and can be varied depending upon the application. The proximal end portion 114 of the sheath 110 and the proximal end portion 118 of the imaging core 112 are connected to the interface module 104. The proximal end portions 114, 118 are fitted with a catheter hub 124 that is removably connected to the interface module 104. The catheter hub 124 facilitates and supports a rotational interface that provides electrical and mechanical coupling between the catheter 102 and the interface module 104.

The distal end portion 120 of the imaging core 112 includes a transducer assembly 122. The transducer assembly 122 is configured to be rotated (either by use of a motor or other rotary devices or methods) to obtain images of the vessel. The transducer assembly 122 can be of any suitable type for visualizing a vessel and, in particular, a stenosis in a vessel. In the depicted embodiment, the transducer assembly 122 includes a piezoelectric micromachined ultrasonic transducer ("PMUT") transducer and associated circuitry, such as an application-specific integrated circuit (ASIC). An exemplary PMUT used in IVUS catheters may include a polymer piezoelectric membrane, such as that disclosed in U.S. Pat. No. 6,641,540, hereby incorporated by reference in its entirety. The PMUT transducer can provide greater than 75% bandwidth for optimum resolution in a radial direction, and a spherically-focused aperture for optimum azimuthal and elevation resolution.

The transducer assembly 122 may also include a housing having the PMUT transducer and associated circuitry disposed therein, where the housing has an opening that ultrasound signals generated by the PMUT transducer travel through. Alternatively, the transducer assembly 122 includes a capacitive micromachined ultrasonic transducer ("CMUT"). In yet another alternative embodiment, the transducer assembly 122 includes an ultrasound transducer array (for example, arrays having 16, 32, 64, or 128 elements are utilized in some embodiments).

The rotation of the imaging core 112 within the sheath 110 is controlled by the interface module 104, which provides user interface controls that can be manipulated by a user. The interface module 104 can receive, analyze, and/or display information received through the imaging core 112. It will be appreciated that any suitable functionality, controls, information processing and analysis, and display can be incorporated into the interface module 104. In an example, the interface module 104 receives data corresponding to ultrasound signals (echoes) detected by the imaging core 112 and forwards the received echo data to the control system 106. In an example, the interface module 104 performs preliminary processing of the echo data prior to transmitting the echo data to the control system 106. The interface module 104 may perform amplification, filtering, and/or aggregating of the echo data. The interface module 104 can also supply high- and low-voltage DC power to support operation of the catheter 102 including the circuitry within the transducer assembly 122.

In some embodiments, wires associated with the IVUS imaging system 100 extend from the control system 106 to the interface module 104 such that signals from the control system 106 can be communicated to the interface module 104 and/or vice versa. In some embodiments, the control system 106 communicates wirelessly with the interface module 104. Similarly, it is understood that, in some embodiments, wires associated with the IVUS imaging system 100 extend from the control system 106 to the monitor 108 such that signals from the control system 106 can be communicated to the monitor 108 and/or vice versa. In some embodiments, the control system 106 communicates wirelessly with the monitor 108.

An ultrasound transducer can be included in the IVUS imaging system 100, for example in the transducer assembly 122. The ultrasonic transducer has a small size and achieves a high resolution, so that it is well suited for intravascular imaging. In some embodiments, the ultrasonic transducer has a size on the order of tens or hundreds of microns, can operate in a frequency range between about 1 mega-Hertz (MHz) to about 135 MHz, and can provide sub 50 micron resolution while providing depth penetration of at least 10 millimeters (mm). Furthermore, the ultrasonic transducer is also shaped in a manner to allow a developer to define a target focus area based on a deflection depth of a transducer aperture, thereby generating an image that is useful for defining vessel morphology, beyond the surface characteristics. The various aspects of the ultrasound transducer and its fabrication are discussed in greater detail below.

In certain embodiments, the ultrasound transducer is a piezoelectric micromachined ultrasound transducer (PMUT). In other embodiments, the transducer may include an alternative type of transducer. Additional features can be added in the ultrasound transducer, and some of the features described below can be replaced or eliminated for additional embodiments of the ultrasound transducer. For additional details of fabricating such ultrasonic transducer, refer to U.S. Provisional Application 61/745,212, titled "Methods and Apparatus for Focusing Miniature Ultrasound Transducers" to Dylan Van Hoven, filed on Dec. 21, 2012, Provisional U.S. Patent Application 61/745,091 to Dylan Van Hoven, filed on December 21, entitled "Preparation and Application of a Piezoelectric Film for an Ultrasound Transducer", and Provisional U.S. Patent Application No. 61/646,080 titled "DEVICE AND SYSTEM FOR IMAGING AND BLOOD FLOW VELOCITY MEASUREMENT" filed on May 11, 2012, Provisional U.S. Patent Application No. 61,646,074 titled "ULTRASOUND CATHETER FOR IMAGING AND BLOOD FLOW MEASUREMENT" filed on May 11, 2012, and Provisional U.S. Patent Application No. 61/646,062 titled "Circuit Architectures and Electrical Interfaces for Rotational Intravascular Ultrasound (IVUS) Devices" filed on May 11, 2012, the contents of each of which are hereby incorporated by reference in their entirety.

Traditionally, the ultrasound transducer is located on a wire-die sub assembly, which means that the electrical and mechanical systems are separate sub-assemblies. This leads to problems such as interconnection reliability, higher costs, more complicated fabrication steps, and inflexible configurability.

According to the various aspects of the present disclosure, provided is a method for attaching two electrical dies by wire bonding and then encasing the assembly in a protective casting that works by arranging two dies into a fixture conducive to wire bonding, but also such that doped epoxy may be immediately dispensed over the assembly to form a near-net-shape protective cover, also known as the Drive Can. By doing so, the present disclosure offers numerous advantages over the prior art. Some of these advantages include:

Mechanical and electrical protection of the ASIC and MEMS interconnection during transport and assembly.
Eliminate stainless steel can component cost.
Integrated assembly reduces steps and variation during assembly.
Allows for both flat and angled transducer arrangements.
Can be performed at room temperature.

The method steps of the present disclosure are now discussed in more detail in view of FIGS. 2-8, which contain illustrations of the can and wire bonding mixture and casting mold.

According to the various aspects of the present disclosure, several steps are performed to create the assembly. First, the dies are loaded into a fixture. Next, dies are wire bonded. Thereafter, epoxy is injected into the tool. In some embodiments, this step can also be partially done as a first step. Next, epoxy is cured. Afterwards, the parts are ejected from the tool. Thereafter, wires are attached. Conformal coating (e.g., Paralyne) is then performed to the "tadpole assembly." Lastly, the tadpole is threaded into Drive Cable, and the Cast Can is then attached to the Drive Cable.

To create the wire bond, these following steps may be performed:
1. The fixture 400 shown in FIG. 6 is opened up, and custom dies, including a MEMS transducer 210 and an ASIC 220, are placed into their specific pockets in the core (bottom) side (also referred to as the bottom plate 410 in some instances) of the fixture 400.
2. The Wire Bonding Plate A 440 is assembled and the plate 440 retained by a fastening method, thereby trapping the dies in a fixed position. FIG. 9 shows a side view of the Wire Bonding Plate A 440 along with the lower half of the mold.
3. A commercially available wire bonder is used to electrically attach the dies.
4. A thin protective coating, such as a parylene coating 250, is applied over the wires 240 to protect them from the casting process and from any shrinking of the epoxy during curing that might dislodge the wire or lift the pads 225.
5. The Wire Bonding Plate A 440 is removed.

Figure 8:
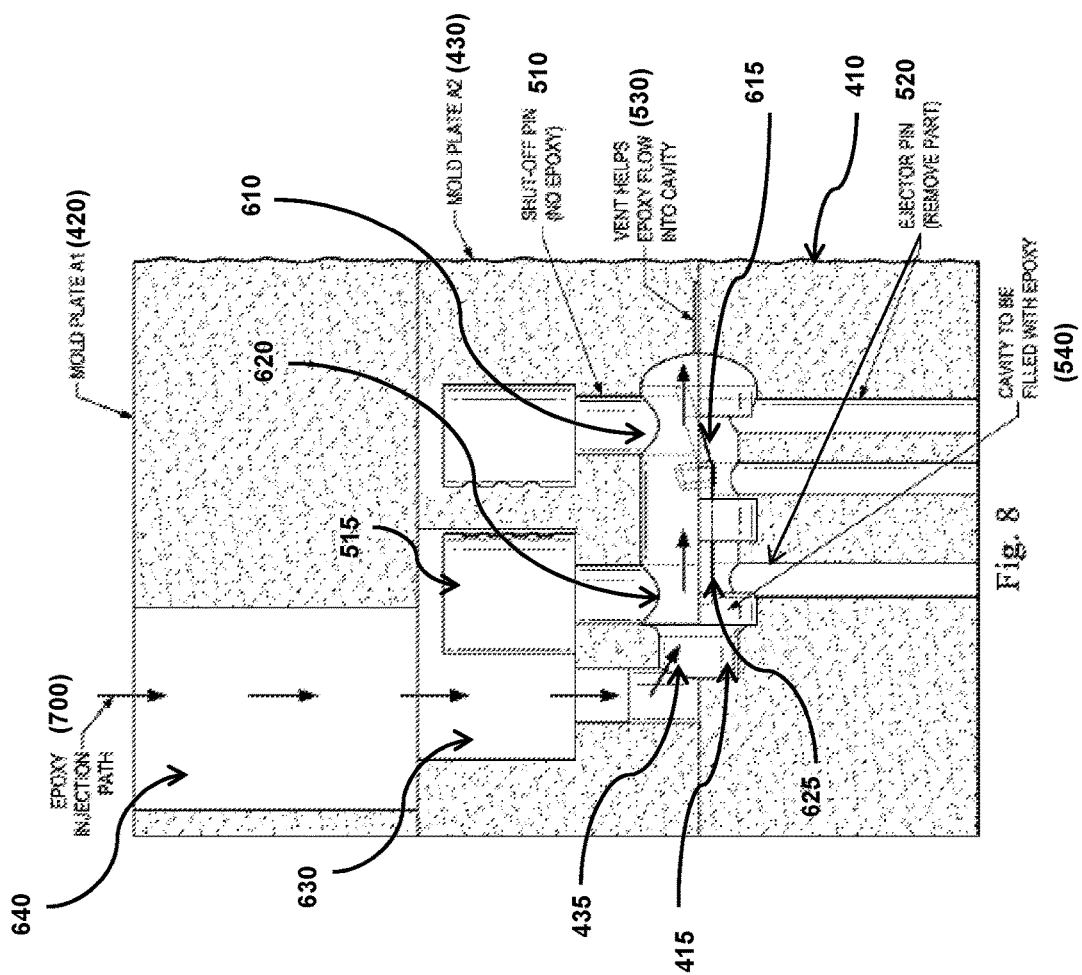

To create the Cast Can 200, these following steps may be performed:
1. The Casting plates A1 420 and A2 430, also referred to as mold plate A1 420 and mold plate A2 430 or molding plate A1 420 and molding plate A2 430 in some instances, are placed and retained as shown in FIG. 8.
2. Epoxy is injected into the open port 700 of each cavity. The vent gap 530 at the distal end of the flow aids in the flow of epoxy. A stylized version of the cast can 200 in the mold is shown in FIG. 7.
3. The Epoxy is allowed to cure, generally in an oven (60 C) for 2 to 8-hours.
4. The Casting plates A1 420 and A2 430 are removed.
5. The finger-shaped ejector plate is slid out allowing the cavity to drop down in its place.
6. The dropping cavity plate separates the cast parts, which are held up on the ejector pins 520.
7. The cast parts are carefully removed from the ejector pins 520.

FIGS. 2-4 show various views of the injection molded can 200 over molded on the transducer 210 and ASIC assembly 220.

In reference to drawing FIG. 5, the following steps may then be performed next:
1. After casting the wires 240 can be welded to the ASIC 220, and the sub-assembly placed in a vacuum deposition parylene coater.
2. The Drive Cable 300 is then glued to the base of the Cast Can 200.
3. In another preferred method, the wires 240 are already attached to the ASIC 220 and the Drive Cable 300 is over-molded by the epoxy in the tool.

Among other things, at least the following elements of the present disclosure are believed to be novel:
1. Casting a doped epoxy can over a wire-bonded assembly.

2. Casting a doped epoxy can over an angled wire-bonded assembly.
3. Using shut-off pins 510 to protect the transducer surface and cable attachment pads 225.
4. Using high lubricity plating on the tool to insure easy ejection.
5. Using ejector pins 520 to separate the case part from the tool.
6. Using a distal vent 530, also referred to as the vent gap 530 in some instances, to draw epoxy into the tool. (A vacuum may be applied.)
7. Conformal coating the cast epoxy can 200.
8. Attaching the cast can 200 to a Drive Cable 300.

A bonding apparatus for bonding a plurality of electrical dies, comprising: a bottom plate 410 that includes a first cavity 415, wherein the first cavity 415 includes a first pocket 615 configured to accommodate a Piezoelectric Micromachined Ultrasound Transducer (PMUT) die 210 and a second pocket 625 configured to accommodate an Application Specific Integrated Circuit (ASIC) die 220; a bonding plate 440 configured to be positioned over and against the bottom plate 410, the bonding plate 440 including a recess, wherein when the bonding plate 440 is positioned against the bottom plate 410: the PMUT die 210 and the ASIC die 220 would be trapped in a fixed position; and the recess exposes a portion of the first pocket 615 and a portion of the second pocket 625; a molding plate 430 configured to be positioned over and against the bottom plate, wherein the molding plate 430 includes: a second cavity 435 that is aligned with the first cavity 415 when the molding plate 430 is positioned against the bottom plate 410, such that the first and second cavities 415 and 435 collectively define a shape of a transducer assembly; a first opening 610 that is coupled to the second cavity 435, wherein the first opening 610 exposes a portion of the first pocket 615 when the molding plate 430 is positioned against the bottom plate 410; a second opening 620 that is coupled to the second cavity 435, wherein the second opening 620 exposes a portion of the second pocket 625 when the molding plate 430 is positioned against the bottom plate 410; and a third opening 630 that is in fluid communication with the first and second cavities 415 and 435 such that a fluid can flow into the first and second cavities 415 and 435 through the third opening 630.

The bonding apparatus, further comprising a first shut-off pin 510 configured to be positioned inside the first opening 610 of the molding plate 430 such that, when the molding plate 430 is positioned against the bottom plate 410, the first shut-off pin 510 makes physical contact with an upper surface of the PMUT die 210. The bonding apparatus, further comprising a second shut-off pin 515 configured to be positioned inside the second opening 620 of the molding plate 430 such that, when the molding plate 430 is positioned against the bottom plate 410, the second shut-off pin 515 makes physical contact with an upper surface of the ASIC die 220. The bonding apparatus, wherein the molding plate further includes a vent gap 530 that is in fluid communication with the second cavity 435. The bonding apparatus, wherein the molding plate 430 is a first molding plate, and further comprising a second molding plate 420 that is configured to be positioned over and against the first molding plate 430, wherein the second molding plat 420 includes a fourth opening 640 that is in fluid communication with the third opening 630. The bonding apparatus, wherein transducer assembly has a curved tip. The bonding apparatus, wherein the curved tip is located proximate to the PMUT die 210 and has a spherical shape. The bonding apparatus, wherein the recess of the bonding plate 430 is configured to allow for an electrical connection between the PMUT die 210 and the ASIC die 220. The bonding apparatus, wherein the electrical connection comprises a bond wire 230.

An ultrasound transducer assembly, comprising: a Piezoelectric Micromachined Ultrasound Transducer (PMUT) die 210 that includes a PMUT device 210; an Application Specific Integrated Circuit (ASIC) die 220 that is physically separated from the PMUT die 210, the ASIC die 220 including a plurality of conductive terminals; a conductive element that electrically couples the PMUT die 210 and the ASIC die 220 together; a packaging material that encapsulates the conductive element and partially encapsulates the PMUT die 210 and the ASIC die 220 therein, wherein the packaging material has a substantially uniform material composition throughout and includes a first opening 610 that exposes a surface of the PMUT device 210, and wherein the packaging material supports the PMUT die 210 and the ASIC die 220 in a fixed position relative to each other and defines an outer surface of the ultrasound transducer assembly.

The ultrasound transducer assembly, wherein the packaging material is epoxy. The ultrasound transducer assembly, wherein the conductive element comprises a bond wire 230. The ultrasound transducer assembly, further comprising a protective layer 250 coated around the bond wire 230. The ultrasound transducer assembly, further comprising a layer conformally coated around the packaging material. The ultrasound transducer assembly, wherein the layer contains parylene. The ultrasound transducer assembly, further comprising wires 240 attached to a drive cable 300, wherein the wires 240 are electrically coupled to the ASIC die 220. The ultrasound transducer assembly, wherein the packaging material includes a second opening 620 that at least partially exposes the conductive terminals. The ultrasound transducer assembly, wherein the packaging material has a rounded tip near the PMUT die 210.

A method of fabricating an ultrasound transducer assembly, comprising: loading a Piezoelectric Micromachined Ultrasound Transducer (PMUT) die 210 and an Application Specific Integrated Circuit (ASIC) die 220 in a first pocket 615 and a second pocket 625 of a first cavity 415 of a bottom plate 410; positioning a bonding plate 440 over and against the bottom plate 410 in a manner such that the PMUT die 210 and the ASIC die 220 are held in a fixed position, wherein the bonding plate 410 includes a recess that exposes portions of the PMUT die 210 and the ASIC die 220; placing a conductive element in the recess, the conductive element electrically interconnecting the PMUT die 210 and the ASIC die 220; thereafter removing the bonding plate 440; positioning a molding plate 430 over and against the bottom plate 410 in a manner such that a second cavity 435 of the molding plate 430 is aligned with the first cavity 415 of the bottom plate 410, wherein the first and second cavities 415 and 435 collectively define a shape of the ultrasound transducer assembly; injecting a packaging material into the first and second cavities 415 and 435 through a first opening 630 of the molding plate 430 that is in fluid communication with the first and second cavities 415 and 435, the packaging material encapsulating the conductive element and at least partially encapsulating the PMUT die 210 and the ASIC die 220 therein; and curing the packaging material, thereby forming the ultrasound transducer assembly, wherein the cured packaging material defines an outer surface of the ultrasound transducer assembly.

The method, wherein the packaging material comprises epoxy. The method, wherein the molding plate 430 includes a second opening 610 that exposes a portion of the PMUT die 210 when the molding plate 430 is positioned against the bottom plate 440, and further comprising: placing a shut-off pin 510 in the second opening 610 during the injecting so as to prevent the packaging material from coming into contact with a surface of the PMUT die 210. The method, wherein the molding plate 430 includes a third opening 620 that exposes a portion of the ASIC die 220 when the molding plate 430 is positioned against the bottom plate 410, and further comprising: placing a further shut-off pin 515 in the third opening 620 during the injecting so as to prevent the packaging material from coming into contact with a surface of the ASIC die 220. The method, wherein the placing the conductive element comprises wire-bonding the PMUT die 210 and the ASIC die 220. The method, further comprising: applying a protective coating 250 around the conductive element in the recess before the removing of the bonding plate 440. The method, further comprising: removing the transducer assembly; applying a parylene coating 250 around the transducer assembly; and attaching the transducer assembly to a drive cable 300.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus for fabricating an ultrasound transducer assembly, comprising:
    a bottom plate that includes a first cavity, wherein the first cavity includes a first pocket configured to accommodate an ultrasound transducer die and a second pocket configured to accommodate an Application Specific Integrated Circuit (ASIC) die;
    a bonding plate configured to be selectively positioned over and against the bottom plate, the bonding plate including a recess, wherein when the bonding plate is positioned against the bottom plate:
        the ultrasound transducer die and the ASIC die would be trapped in a fixed position, and
        the recess exposes a portion of the first pocket and a portion of the second pocket;
    a molding plate configured to be selectively positioned over and against the bottom plate after the bonding plate has been removed, wherein the molding plate includes:
        a second cavity that is aligned with the first cavity when the molding plate is positioned against the bottom plate, such that the first and second cavities collectively define a shape of a transducer assembly,
        a first opening that is coupled to the second cavity, wherein the first opening exposes a portion of the first pocket when the molding plate is positioned against the bottom plate,
        a second opening that is coupled to the second cavity, wherein the second opening exposes a portion of the second pocket when the molding plate is positioned against the bottom plate, and
        a third opening that is in fluid communication with the first and second cavities such that a fluid can flow into the first and second cavities through the third opening; and
    a first shut-off pin configured to be positioned inside the first opening of the molding plate such that, when the molding plate is positioned against the bottom plate, the first shut-off pin makes physical contact with an upper surface of the ultrasound transducer die, wherein the first shut-off pin extends beyond the second cavity.

2. The apparatus of claim 1, further comprising a second shut-off pin configured to be positioned inside the second opening of the molding plate such that, when the molding plate is positioned against the bottom plate, the second shut-off pin makes physical contact with an upper surface of the ASIC die.

3. The apparatus of claim 2, wherein the second shut-off pin extends beyond the second cavity.

4. The apparatus of claim 1, wherein the molding plate further includes a vent gap that is in fluid communication with the second cavity.

5. The apparatus of claim 1, wherein the molding plate is a first molding plate, and further comprising a second molding plate that is configured to be positioned over and against the first molding plate, wherein the second molding plate includes a fourth opening that is in fluid communication with the third opening.

6. The apparatus of claim 1, wherein the transducer assembly has a curved tip.

7. The apparatus of claim 6, wherein the curved tip is located proximate to the ultrasound transducer die and has a spherical shape.

8. The apparatus of claim 1, wherein the recess of the bonding plate is configured to allow for an electrical connection between the ultrasound transducer die and the ASIC die.

9. The apparatus of claim 8, wherein the electrical connection comprises a bond wire.

10. The apparatus of claim 1, further comprising a second ejector pin in contact with a back surface of the ASIC die.

11. The apparatus of claim 1, wherein the ultrasound transducer die comprises a Piezoelectric Micromachined Ultrasound Transducer (PMUT) die.

12. The apparatus of claim 1, wherein the ultrasound transducer die comprises a Capacitive Micromachined Ultrasound Transducer (CMUT) die.

13. The apparatus of claim 1, further comprising a first ejector pin in contact with a back surface of the ultrasound transducer die.

14. An apparatus for fabricating an ultrasound transducer assembly, comprising:
    a bottom plate that includes a first cavity, wherein the first cavity includes a first pocket configured to accommodate an ultrasound transducer die and a second pocket configured to accommodate an Application Specific Integrated Circuit (ASIC) die;
    a bonding plate configured to be selectively positioned over and against the bottom plate, the bonding plate including a recess, wherein when the bonding plate is positioned against the bottom plate:
        the ultrasound transducer die and the ASIC die would be trapped in a fixed position, and
        the recess exposes a portion of the first pocket and a portion of the second pocket;

a molding plate configured to be selectively positioned over and against the bottom plate after the bonding plate has been removed, wherein the molding plate includes:
- a second cavity that is aligned with the first cavity when the molding plate is positioned against the bottom plate, such that the first and second cavities collectively define a shape of a transducer assembly,
- a first opening that is coupled to the second cavity, wherein the first opening exposes a portion of the first pocket when the molding plate is positioned against the bottom plate,
- a second opening that is coupled to the second cavity, wherein the second opening exposes a portion of the second pocket when the molding plate is positioned against the bottom plate, and
- a third opening that is in fluid communication with the first and second cavities such that a fluid can flow into the first and second cavities through the third opening; and a first ejector pin in contact with a back surface of the ultrasound transducer die.

15. The apparatus of claim 14, further comprising a first shut-off pin configured to be positioned inside the first opening of the molding plate such that, when the molding plate is positioned against the bottom plate, the first shut-off pin makes physical contact with an upper surface of the ultrasound transducer die.

16. The apparatus of claim 15 wherein the first shut-off pin extends beyond the second cavity.

17. The apparatus of claim 14, further comprising a second ejector pin in contact with a back surface of the ASIC die.

18. The apparatus of claim 14, further comprising a second shut-off pin configured to be positioned inside the second opening of the molding plate such that, when the molding plate is positioned against the bottom plate, the second shut-off pin makes physical contact with an upper surface of the ASIC die.

19. The apparatus of claim 18, wherein the second shut-off pin extends beyond the second cavity.

20. The apparatus of claim 14, wherein the molding plate further includes a vent gap that is in fluid communication with the second cavity.

21. The apparatus of claim 14, wherein the molding plate is a first molding plate, and further comprising a second molding plate that is configured to be positioned over and against the first molding plate, wherein the second molding plate includes a fourth opening that is in fluid communication with the third opening.

22. The apparatus of claim 14, wherein the recess of the bonding plate is configured to allow for an electrical connection between the ultrasound transducer die and the ASIC die.

23. The apparatus of claim 22, wherein the electrical connection comprises a bond wire.

24. The apparatus of claim 14, wherein the transducer assembly has a curved tip.

25. The apparatus of claim 24, wherein the curved tip is located proximate to the ultrasound transducer die and has a spherical shape.

26. The apparatus of claim 14, wherein the ultrasound transducer die comprises a Piezoelectric Micromachined Ultrasound Transducer (PMUT) die.

27. The apparatus of claim 14, wherein the ultrasound transducer die comprises a Capacitive Micromachined Ultrasound Transducer (CMUT) die.

* * * * *